United States Patent
Dumitrescu et al.

[11] Patent Number: 6,156,275
[45] Date of Patent: *Dec. 5, 2000

[54] SAMPLE TUBE RACK

[75] Inventors: Nicolae Dumitrescu, Stamford; Irena Makarchuk, Fairfield, both of Conn.

[73] Assignee: Bayer Corporation, Tarrytown, N.Y.

[*] Notice: This patent is subject to a terminal disclaimer.

[21] Appl. No.: 09/113,643

[22] Filed: Jul. 10, 1998

Related U.S. Application Data

[63] Continuation-in-part of application No. 08/978,715, Nov. 26, 1997.

[51] Int. Cl.[7] .................................. B01L 9/06; B01L 3/00; A47G 29/00; A47B 73/00
[52] U.S. Cl. ......................... 422/104; 422/99; 211/71.01; 211/74
[58] Field of Search .............................. 422/99, 104, 297, 422/300; 211/71, 71.01, 74

[56] References Cited

U.S. PATENT DOCUMENTS

| | | |
|---|---|---|
| 1,549,111 | 8/1925 | Grollman . |
| 1,634,953 | 6/1927 | McCune et al. ........................ 422/104 |
| 2,467,873 | 4/1949 | Weir . |
| 2,708,037 | 5/1955 | Planeta . |
| 2,741,913 | 4/1956 | Dovas ......................................... 73/61 |
| 3,109,084 | 10/1963 | Walsh . |
| 3,186,556 | 6/1965 | Forsstrom . |
| 3,698,563 | 10/1972 | Gordon et al. . |
| 3,765,538 | 10/1973 | Kowert . |
| 3,905,482 | 9/1975 | Knulst . |
| 4,207,289 | 6/1980 | Weiss . |
| 4,422,555 | 12/1983 | Jacobs . |
| 4,510,119 | 4/1985 | Hevey . |
| 4,534,465 | 8/1985 | Rothermel et al. . |
| 5,137,693 | 8/1992 | Mawhirt ................................... 422/104 |
| 5,186,339 | 2/1993 | Heissler . |
| 5,378,433 | 1/1995 | Duckett et al. . |
| 5,959,221 | 9/1999 | Boyd et al. ............................. 422/104 |

*Primary Examiner*—Jill Warden
*Assistant Examiner*—Dwayne K. Handy
*Attorney, Agent, or Firm*—Andrew L. Klawitter, Esq.; Rodman & Rodman

[57] ABSTRACT

A sample rack for holding sample tubes in a single row includes a frame having a longitudinally extending vertical rear wall and a horizontal top wall. The top wall includes a plurality of sample tube openings. A plurality of vertical partitions and opposite end walls are joined to the frame in spaced arrangement to define sample tube chambers for receiving sample tubes. A front marginal section of the frame connects the bottom portions of vertical partitions and a leaf spring device is attached to the marginal section. The leaf spring device includes a support section and a plurality of arms that extend upwardly from the support section into the sample tube chambers.

20 Claims, 9 Drawing Sheets

SAMPLE TUBE RACK

This application is a continuation-in-part of application Ser. No. 08/978,715, filed Nov. 26, 1997.

BACKGROUND OF THE INVENTION

This invention relates to a rack for sample tubes and, more particularly, to a sample tube rack for tubes of different size that can be automatically transported at a rapid rate in a sample analysis system.

In automated sampling systems, sample tubes are usually transported from one location to another in order to conveniently position the tubes for one or more functional operations on the samples contained therein. Because of the demand for increased test output of automated sampling systems, it often becomes necessary to simultaneously transport a plurality of tubes for test purposes.

Although sample tube racks for holding more than one sample tube are known, such racks are often not feasible for automatic transport in a sample analysis system because they can become unstable during movement. As demand increases for high volume test output of sample analysis systems, there has been an emphasis on increasing the speed of processing of the samples within the system. If sample tube racks are used to transport two or more tubes simultaneously, it may be necessary to limit the speed of movement of the rack to assure that the rack remains stable. Also, high speed movement of sample tube racks may necessitate that there be only short time periods during which a rack can be loaded or unloaded. Springs and other detent and holding members within the rack can delay or interfere with the need for quick loading or unloading of tubes relative to the rack.

It is thus desirable to provide a sample tube rack that is stable while undergoing rapid movement within a sample analysis system, permits quick loading and unloading of sample tubes and can accommodate tubes of different size.

OBJECTS AND SUMMARY OF THE INVENTION

Accordingly, it is an object of the invention to provide a novel sample tube rack which can accommodate sample tubes of different size and shape. A further object of the invention is to provide a novel sample tube rack that remains stable while being automatically transported in a sample analysis system. Another object of the invention is to provide a novel sample tube rack which permits quick and easy insertion and removal of sample tubes from the rack. Still another object of the invention is to provide a novel sample tube rack which has as few as two parts, one of which is a plastic housing portion which can be molded in one piece, and the other of which is a biasing spring which can be formed in one piece.

The present invention provides a sample tube rack for holding sample tubes in a single row. In one embodiment of the invention, the rack includes a rear wall and a top wall that form an angle-shaped frame. A plurality of vertical partitions joined to the angle-shaped frame in spaced arrangement define sample tube chambers for receiving sample tubes. At least one front, marginal connecting section connects the bottom portions of two adjacent partitions opposite the rear wall. A leaf spring device is attached to the marginal connecting section. The leaf spring device includes a support section and a plurality of spring arms that extend upwardly from the support section opposite the rear wall and incline into respective tube receiving chambers. The rack includes base flanges for securement to a transport plate.

In another embodiment of the invention, the sample tube rack includes side flanges for securement to a transport device and a collection basin detachably joined to a lower portion of the rack. Actuator members are also formed on the rack to actuate a sample container dispenser when the rack is moved to an actuation position.

In either embodiment of the invention, whether the rack is secured at its base to a transport device or secured at side flanges to a transport device, it can be rapidly transported from one location to another within the sample analysis system. Tubes held by the rack can be easily and quickly loaded into and unloaded from the sample tube chambers of the rack.

BRIEF DESCRIPTION OF THE DRAWINGS

In the accompanying drawings.

Corresponding reference numbers indicate corresponding parts throughout the several views of the drawings.

DETAILED DESCRIPTION

Figure 1:
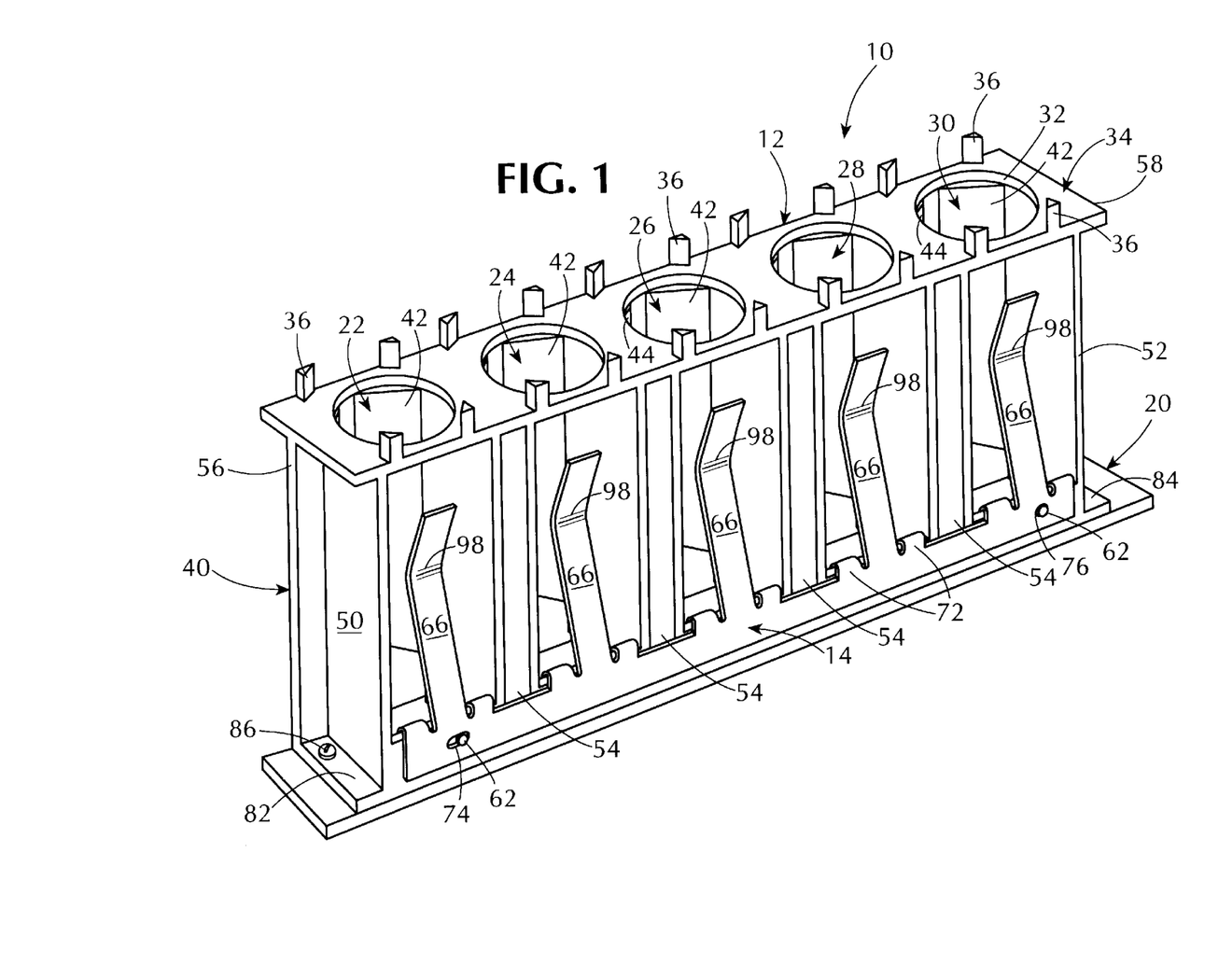
FIG. 1 is a front perspective view of a rack for holding sample tubes incorporating one embodiment of the invention.
Figure 2:
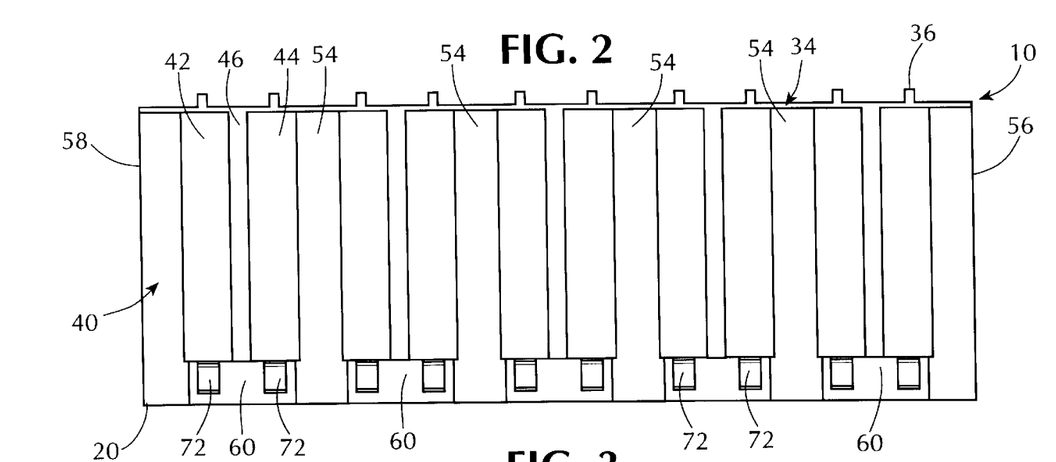
FIG. 2 is a rear elevational view thereof.
Figure 3:
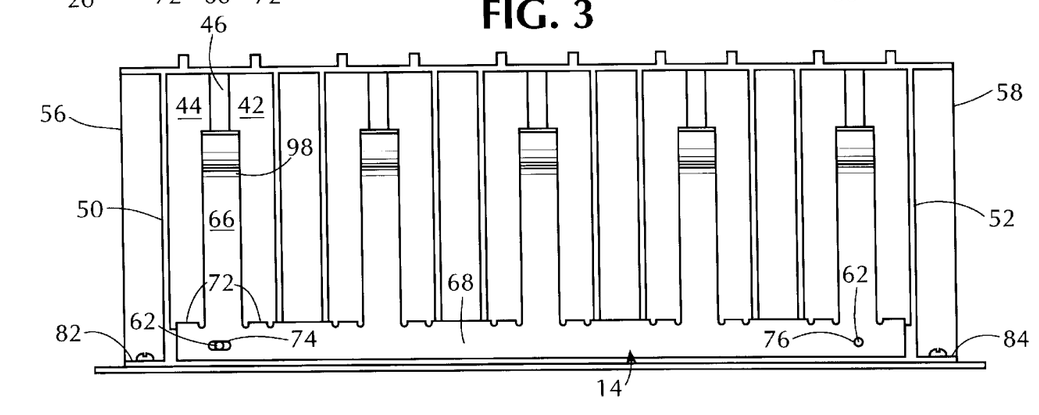
FIG. 3 is a front elevational view thereof.
Figure 4:
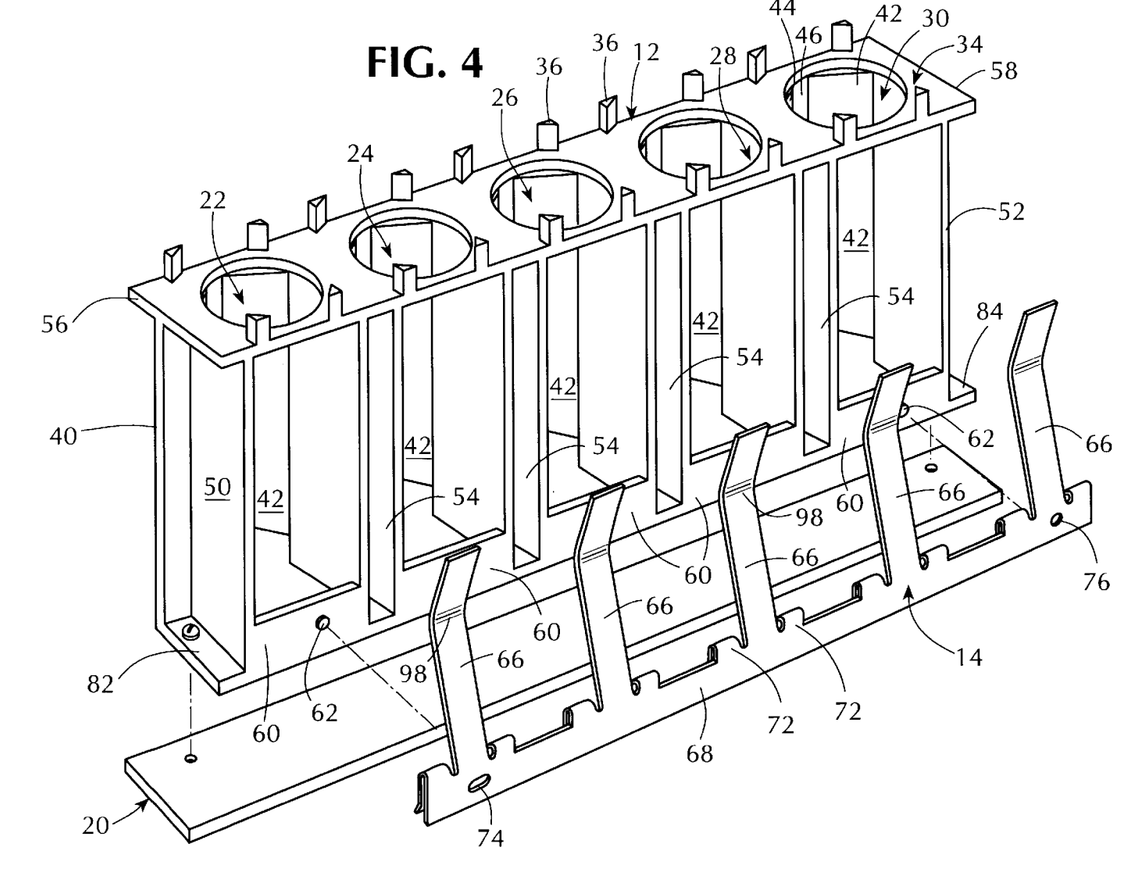
FIG. 4 is an exploded view thereof.

Referring to the drawings, a sample rack incorporating one embodiment of the invention is generally indicated by the reference number 10. Referring to FIGS. 1 and 4, the rack 10 includes a housing shell or frame 12 and a spring component or leaf spring device 14. The rack 10 is supported on a transport plate 20 that is arranged to move the rack and forms no part of the present invention.

The housing shell 12 includes sample tube chambers 22, 24, 26, 28 and 30 which have chamber openings 32 in an elongated top wall 34. A set of four equally spaced confinement prongs 36 project from the top wall 34 around the periphery of each of the five chamber openings 32.

Figure 5:
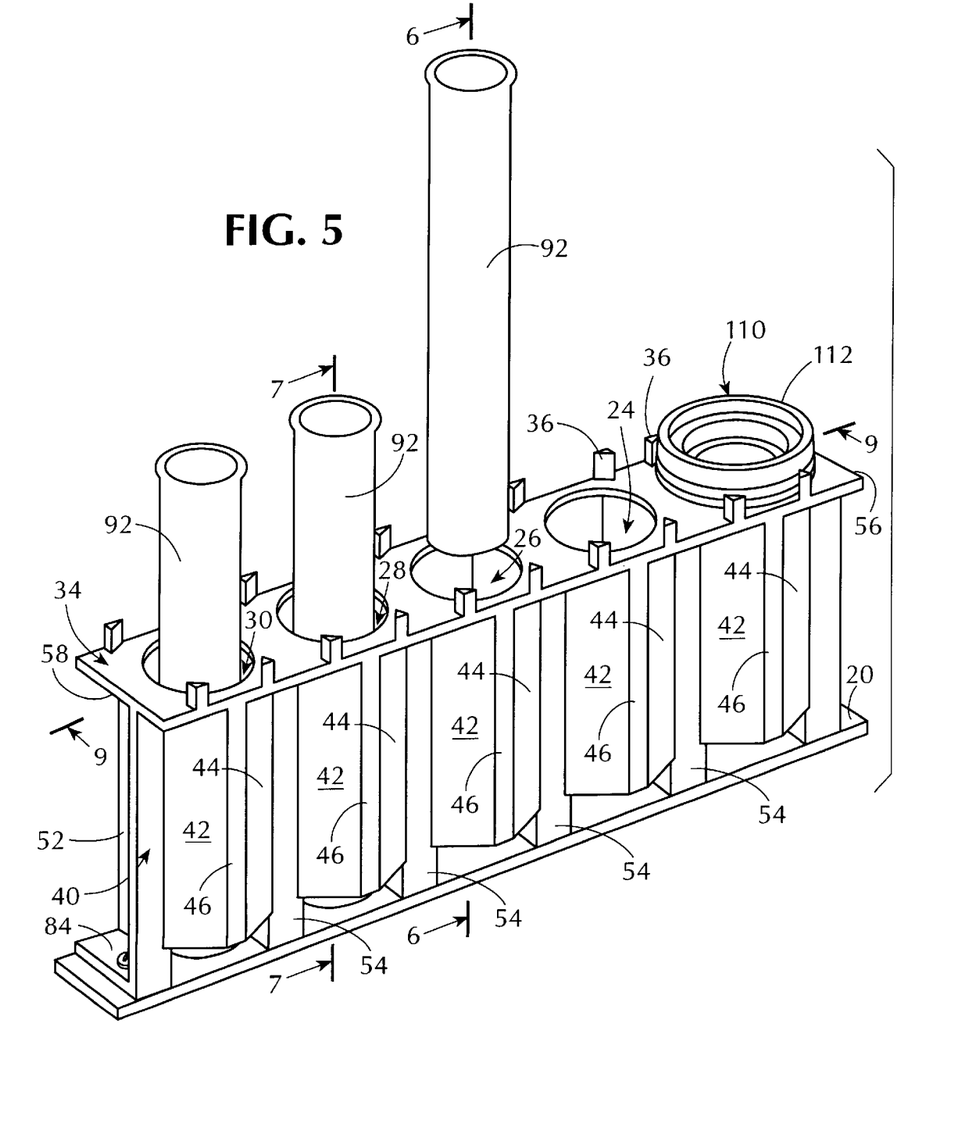
FIG. 5 is a rear perspective view thereof with associated sample tubes.
Figure 6:
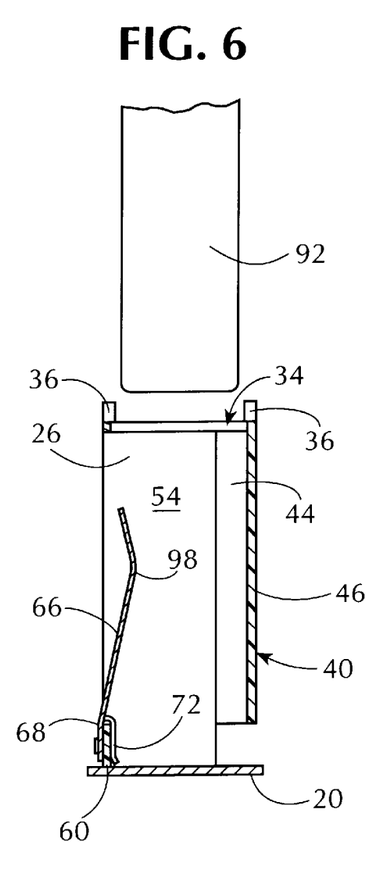
FIG. 6 is a sectional view taken on the line 6—6 of FIG. 5.

A rear wall 40 (FIG. 5) depends from the top wall 34 such that the walls 34 and 40 form an upside down "L" or right angle as shown in FIG. 6. The rear wall 40 includes five spaced sets of converging wall sections 42 and 44 that converge to a flat apex section 46. The wall sections 42, 44 and 46 form the back portion of each of the sample tube chambers 22–30.

As most clearly shown in FIGS. 1 and 4, a small portion of the wall sections 42 and 44 extends within the periphery of the chamber openings 32 such that the wall sections 42 and 44 form contact surfaces for sample tubes 92 that are disposed within the chambers 22–30.

The sample tube chambers 22–30 are set apart from each other by four double wall partitions 54 spaced between end walls 50 and 52 provided at opposite ends of the rack 10. The end walls 50, 52 and the double wall partitions 54 extend below the wall sections 42, 44 and 46 as most clearly shown in FIGS. 4 and 5. The end walls 50 and 52 are slightly recessed from the extreme opposite ends 56 and 58 of the housing shell 12.

Referring to FIG. 4, a front marginal connecting section 60 is provided at the bottom portion of each chamber 22–30. One connecting section 60 with a spring securement pin 62 joins the end wall 50 and the double wall partition 54 of the chamber 22. Another connecting section 60 with a spring securement pin 62 joins the end wall 52 and the partition 54 of the chamber 30. Three other connecting sections 60 join the four double wall partitions 54 that form the side walls of the chambers 24, 26 and 28. The connecting sections 60 collectively form a lower front marginal strip of the housing shell 12.

The spring component 14 includes five spaced spring arms 66 joined at one end to a common support section 68. A pair of bent over clips 72 that extend from the support 68 are provided on opposite sides of each spring arm 66. An elongated slot 74 is provided at one end of the support 68 and a round opening 76 is provided at the opposite end of the support.

The spring component 14 is assembled to the frame 12 by engaging the clips 72 onto the connecting sections 60 such that the spring securement pins 62 at each end connecting section 60 are located in the openings 74 and 76 of the spring support section 68. The clips 72 snugly grip the connecting sections 60 of the housing shell 12. The spring securement pins 62 and the openings 74 and 76 maintain alignment of the spring component 14 on the housing shell 12 such that each spring arm 66 is aligned with each respective sample tube chamber 22–30. The spring arms 66 thus extend upwardly in an upside down arrangement and are normally biased a predetermined amount into the sample tube chambers 22–30.

In using the rack 10, a pair of base flange portions 82 and 84 at opposite ends of the rack 10 are secured to the transport plate 20 by any suitable means such as screws 86. The transport plate 20 can function as a floor for the rack 10.

Figure 7:
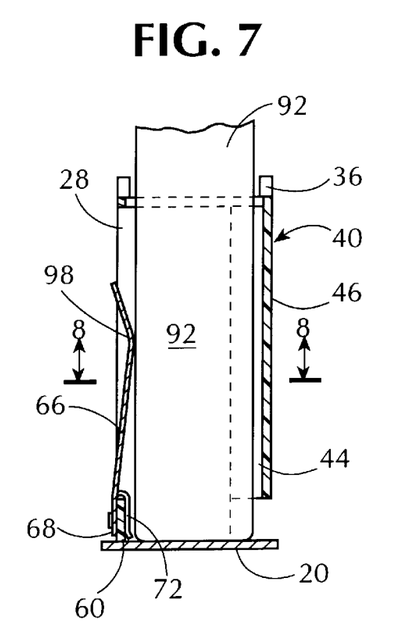
FIG. 7 is a sectional view taken on the line 7—7 of FIG. 5.
Figure 8:
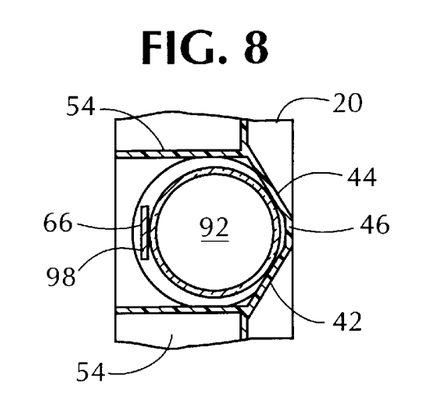
FIG. 8 is a sectional view taken on the line 8—8 of FIG. 7.
Figure 10:
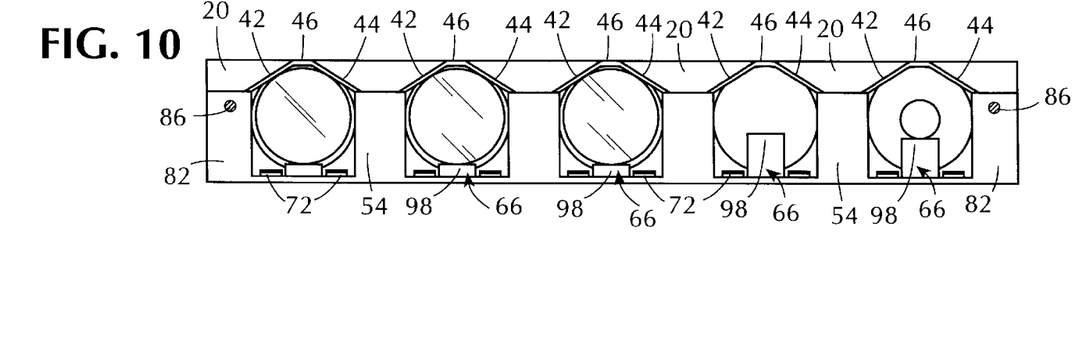
FIG. 10 is a sectional view taken on the line 10—10 of FIG. 9.

Sample tubes such as 92 are disposed in selected chambers such as 26, 28 and 30 (FIG. 5) and engage a bent or contact portion 98 of the biasing spring 66 (FIG. 7) which urge the tubes 92 against the rear wall sections 42 and 44 (FIG. 8). It will be noted that the contact portion 98 is located closer to the free end of the spring arm 66 than the spring support section 68. Furthermore the contact portion 98 is positioned to contact the upper half of the sample tube 92 as shown most clearly in FIGS. 7 and 10. Under this arrangement, the force supplied by the springs 66 against the tubes 92 can be predetermined and set to an optimum magnitude that permits easy insertion and removal of sample tubes. Also, the tubes 92 are stabilized in the rack 10 because the detent force supplied by the spring 66 is applied at an upper section of the tube. The tube receiving chambers 22–30 can be sized to accommodate tubes of selected length within a predetermined diametrical range of 13–16 millimeters, for example.

Figure 9:
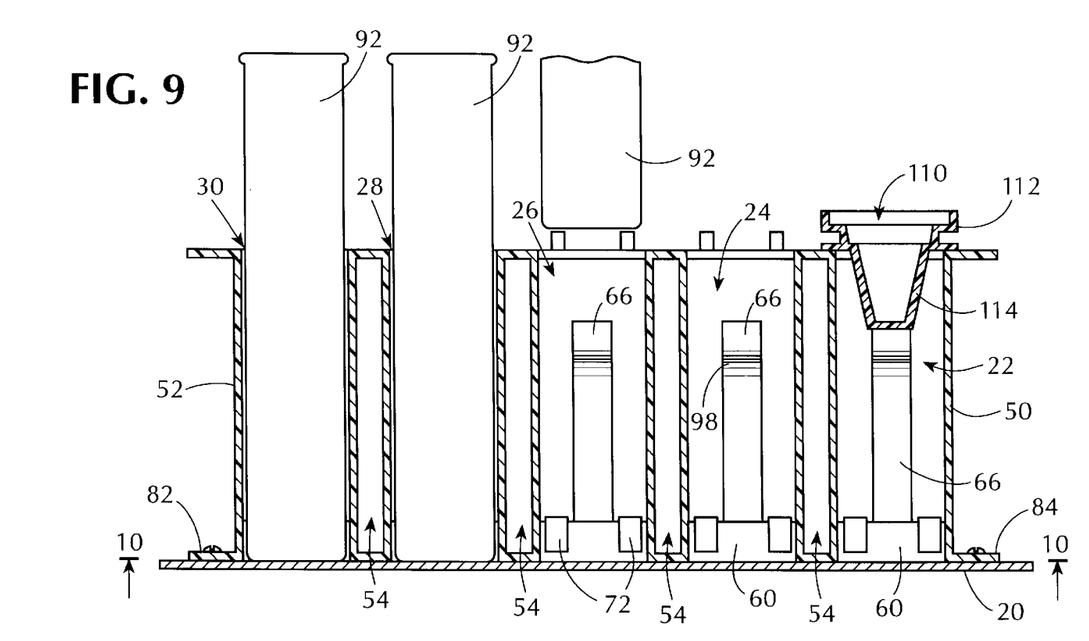
FIG. 9 is a sectional view taken on the line 9—9 of FIG. 5.

The rack 10 can also accommodate relatively small sample tubes 110 (FIGS. 5 and 9), usually referred to as sample cups. The sample cups 110 have a collar portion 112 that fits within the confines of the four prongs 36 that surround the opening 32 of the chamber 22 for example. The cup 110 has a cup portion 114 that depends from the collar 112 into the chamber 22, but not far enough to engage the spring 66.

The rack 10 when secured to the transport plate 20 is maintained in a stable position on the transport plate and moves at the speed of the transport plate. Since the rack 10 is stable when secured to the transport plate 20, the transport plate 20 can provide rapid movement of the rack 10 without upsetting the tubes 92, the sample cups 110 or their contents.

Figure 11:
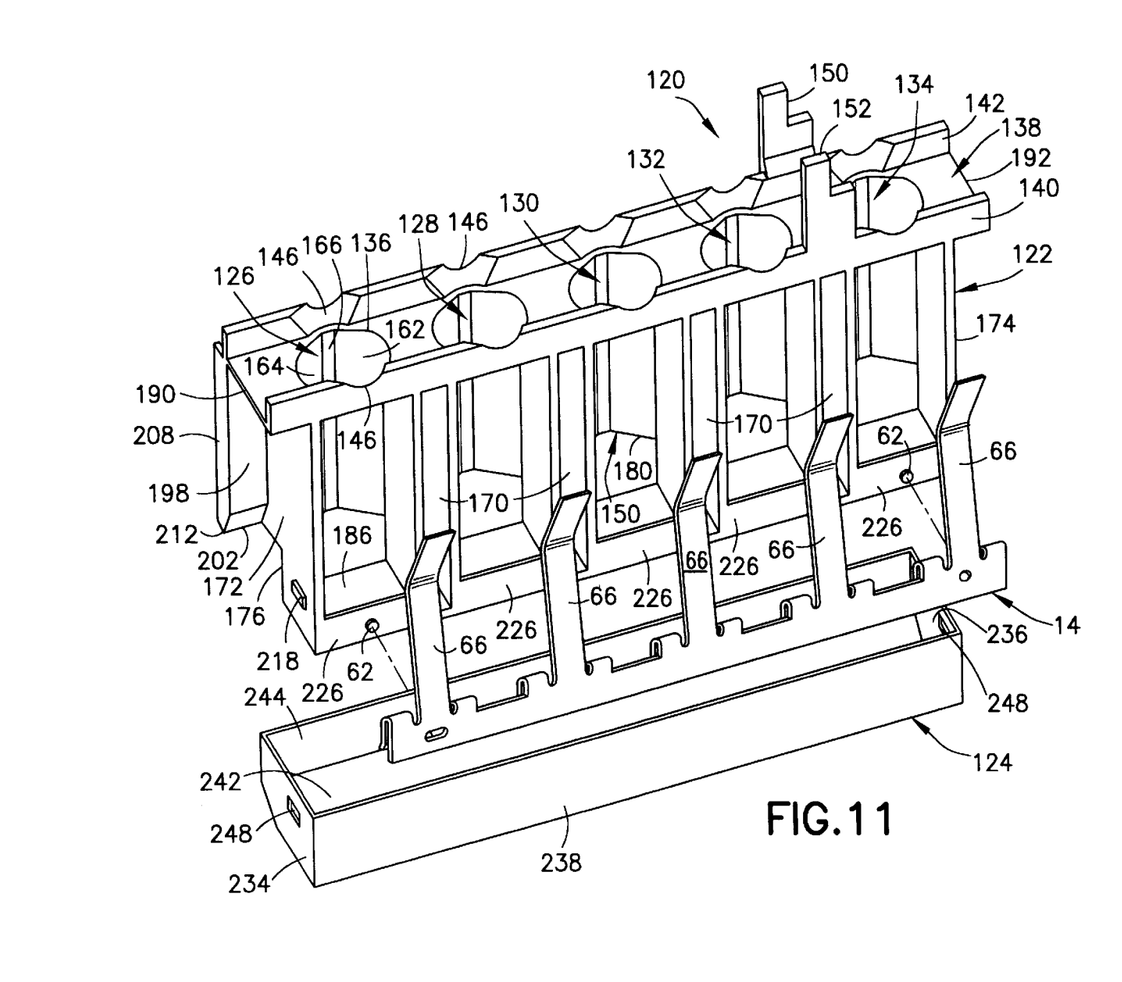
FIG. 11 is an exploded perspective view of another embodiment of the invention.
Figure 12:
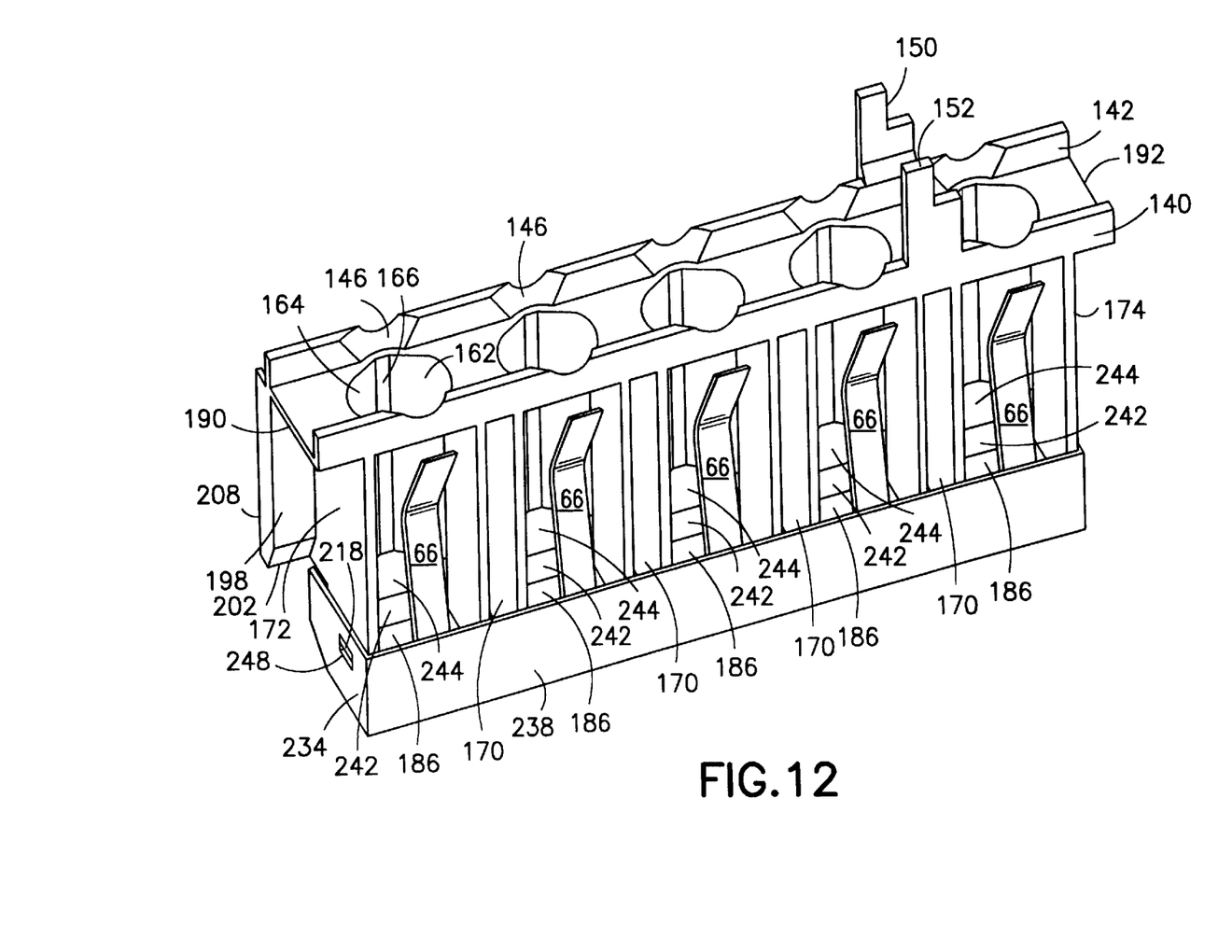
FIG. 12 is a perspective of the assembled components of FIG. 11.
Figures 13, 14:
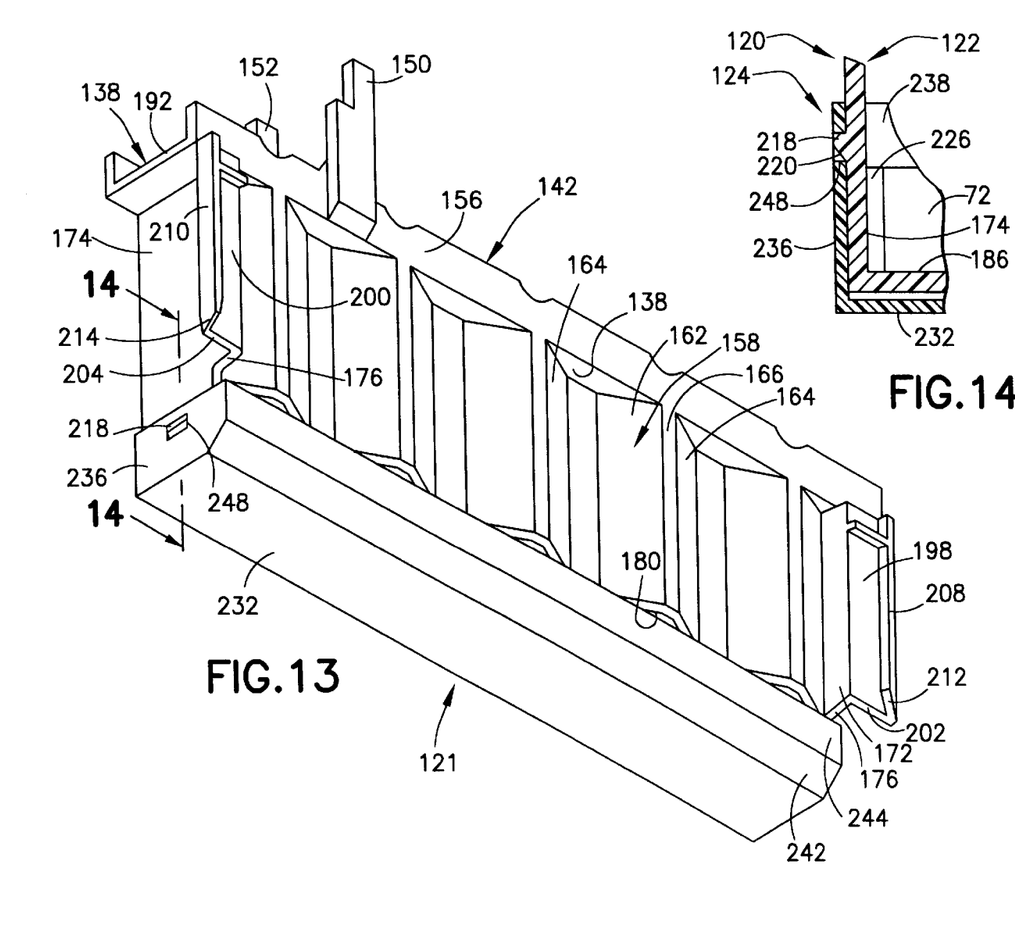
FIG. 13 is a bottom perspective view thereof.
FIG. 14 is a fragmentary sectional view thereof taken on the line 14—14 of FIG. 13.

A sample tube rack incorporating another embodiment of the invention, which is the preferred embodiment, is generally indicated by the reference number 120 in FIGS. 11–13.

The rack 120 includes a housing shell or frame 122, the spring component or leaf spring device 14 and a spill basin member 124.

The housing shell 12 includes sample tube chambers 126, 128, 130, 132 and 134 which have chamber openings 136 in an elongated top wall 138. A pair of spaced riser walls 140 and 142 extend upwardly from the top wall 138 and include curved recesses 146 that align with the respective chamber openings 136. The curved recesses 146 confine the collar portion 112 of a small sample tube 110 of the type shown in FIG. 9, when such sample tube 110 is disposed in a chamber opening 136 of any of the chambers 126–134.

Oppositely disposed actuator fingers 150 and 152 extend upwardly from the riser walls 140 and 142 to actuate a release mechanism (not shown) that dispenses a small sample container 110 into a selected chamber 126–134 of the rack 10. Depending upon the desired spacing between the actuator fingers 150 and 152, the finger 150 can be formed on an outside surface 156 of the riser wall 142 as shown in FIG. 13, while the finger 152 is formed as a smooth continuation of the riser wall 140, as shown in FIG. 11.

A rear wall 158 (FIG. 13) depends from the top wall 138 such that the top wall 138 and the rear wall 158 form an upside down "L" or right angle in the same manner as the top wall 34 and the rear wall 40 of the first embodiment form an upside down "L" as shown in FIG. 6. The rear wall 158 includes five spaced sets of converging wall sections 162 and 164 that converge to a flat apex section 166. The wall sections 162, 164 and 166 form the back portion of each of the sample tube chambers 126–134.

As most clearly shown in FIGS. 11 and 12, a top edge portion of the wall sections 162, 164 and the apex section 166 form a portion of the periphery of the chamber openings 32 such that the wall sections 162 and 164 constitute contact surfaces for a sample tube 92 of the type shown in FIG. 5 that can be disposed within the sample tube chambers 126–134.

The sample tube chambers 126–134 are set apart from each other by four double wall partitions 170 spaced between end walls 172 and 174 provided at opposite end portions of the rack 10. Each of the end walls 172 and 174 include an inward step 176 (FIGS. 11 and 13). The end walls. 172, 174 and the double wall partitions 170 extend below the wall sections 162, 164 and 166 as most clearly shown in FIG. 11. The rear wall 156 thus has a downwardly directed free edge 180 as most clearly shown in FIG. 11. The double wall partition 170 and the end walls 172 and 174 extend downwardly to a base portion 186 which constitutes a floor of the frame 122.

The end walls 172 and 174 are slightly recessed from the extreme opposite end 190 and 192 of the top wall 138. As most clearly shown in FIG. 13 a pair of securement flanges 198 and 200 depend from the end portions 192 and 194 of the top wall 138 at the end walls 172 and 174. The securement flanges 198 and 200 include slightly tapered free edges 202 and 204. Each of the securement flanges 198 and 200 is also formed with a respective stub wall 208 and 210 that have slightly tapered lower end portions 212 and 214.

A latch projection 218 (FIG. 18) is provided on each of the end walls 172 and 174 proximate the base portion 186. As most clearly shown in FIG. 14, the latch projection 218 has a slightly tapered lower surface 220.

Referring to FIG. 11 front marginal wall portions 226 at the bottom portion of each chamber 126–134 extend upwardly from the base portion 186. One marginal wall portion 226 with a spring securement pin 62 joins the end wall 172 and the double wall partition 170 of the chamber 126. Another marginal wall portion 226 with a spring securement pin 62 joins the opposite end wall 174 and the double wall partition 170 of the chamber 134. Three other marginal wall portions 226 join the four double wall partitions 170 that form the sides of the chambers 123, 130 and 132. The marginal wall portions 226 collectively form a lower front marginal strip of the housing shell 122.

The spring component 14 of the rack 120 is identical to the spring component 14 of the rack 10 and is installed in the rack 120 in the same manner as described for the rack 10 to permit the spring arms 66 to extend upwardly in an upside down arrangement into the sample tube chambers 126–134.

The collection basin 124 is formed of a suitable flexible plastic such as Kydex with a wall thickness of approximately one millimeter. The collection basin 124 includes a base portion 232 (FIG. 13), opposite end walls 234, 236, a front wall 238 and a rear wall consisting of an inclined lower rear wall portion 242 and a vertical upper rear wall portion 244. The opposite end walls 234 and 236 are formed with latch openings 248 to receive the latch projection 218 of the rack frame 122.

The collection basin 124 is sized to accommodate the rack frame 122 such that the base portion 186 of the rack frame 122 can seat onto the base portion 232 of the collection basin 124 when the latch projections 218 of the rack frame 122 engage the latch openings 248 of the collection basin 124. Removal of the collection basin 124 from the rack frame 122 is accomplished by slightly squeezing the front wall 238 and the vertical upper wall 244 toward each other at the end walls 234 and 236 to cause the end walls 234 and 236 to belly out and disengage the latch opening 248 from the latch projection 218.

One example of a size relationship between the basin 124 and the rack frame that permits easy insertion and removal of the rack frame 122 from the collection basin 124 is as follows. With regard to the rack frame 122, the outside distance from the end wall 172 to the end wall 174 can be approximately 12.1 centimeters, the width of the base portion 186 can be approximately 1.5 centimeters and the upper edge of the latch projection 218 can be approximately 1.05 centimeters from the bottom 232 and is approximately 2 mm thick in the vertical dimension. With regard to the basin 124, the basin height from the base 232 to the top free edges can be approximately 1.35 centimeters, the outside distance from the end wall 234 to the end wall 236 can be approximately 12.2 centimeters and the inside distance between the front wall 238 and the vertical upper rear wall 244 can be approximately 2 centimeters. The upper edge of the latch opening 248 is approximately 1.15 centimeters from the base 232 and is approximately 2.2 mm wide in the vertical dimension.

In using the rack 120 the rack frame 122 is disposed in the collection basin 124 by simply pushing the collection basin 124 onto the base portion of the rack frame 122 to permit engagement between the latch projection 218 and the latch opening 248 as shown in FIG. 14. The inclined surface 220 of the latch projection 218 facilitates engagement between the latch projection 218 and the latch opening 248. The collection basin 124 is intended to pick up any spillage of ingredients that might issue from sample tubes such as 92 (FIG. 5) that are disposed in the sample tube chambers 126–134. Easy detachability of the collection basin 124 from the rack frame 122 facilitates cleanup of any such spillage.

When it is desired to transport the rack 10, it is placed in an automatic transport device (not shown) wherein the securement flanges 198 and 200 are engageable by gripper fingers of a spring clip or a holding clip (not shown) which detachably grips opposite surfaces of the securement flanges 198 and 200 to hold the rack 120 in a fixed upright position during automatic transport of the rack 120 from one location to another.

The rack 120, when secured to the automatic transport device, is maintained in a stable upright position to provide rapid movement of the rack 120 without upsetting the sample tubes 92 or the sample cups 110 or their contents.

Some advantages of the present invention evident from the foregoing description include a sample rack that accommodates sample tubes of different diameter with a predetermined detent force that permits easy insertion and removal of the sample tubes from the rack. The rack is conveniently secured to a transport plate or the holding clip of a transport device to permit rapid movement of the rack and its contents without upsetting such contents. The upside down arrangement of the sample tube biasing spring and the contact engagement of the biasing spring against the sample tubes at an upper portion of the sample tube facilitates establishment of a biasing force that permits easy loading and unloading of the rack.

In view of the above, it will be seen that the several objects of the invention are achieved, and other advantageous results attained.

As various changes can be made in the above constructions without departing from the scope of the invention, it is intended that all matter contained in the above description or shown in the accompanying drawings shall be interpreted as illustrative and not a limiting sense.

What is claimed is:

1. A sample tube rack, comprising a frame having a top wall, a rear wall depending from said top wall and having a lower free edge, opposite end walls joined to said rear wall and having lower end portions depending from said top wall below the lower free edge of said rear wall, at least one partition member spaced between said end walls to define at least two sample tube chambers, said partition member having a lower end portion depending below the lower free edge of said rear wall, a front lower marginal section joining said end walls and said partition member, and a spring device joined to said front lower marginal section and having individual upwardly extending spring arms each of which is inclined into a respective said sample tube chamber to bias said sample tube chamber toward said rear wall.

2. The sample tube rack as claimed in claim 1, including a plurality of said partitions spaced from each other to define additional ones of said sample tube chambers between consecutively spaced partitions.

3. The sample tube rack as claimed in claim 1, wherein said spring device includes a main support section and said individual upwardly extending spring arms extend from said main support section.

4. The sample tube rack as claimed in claim 3, wherein said individual upwardly extending spring arms are arranged side by side on said main support section.

5. The sample tube rack as claimed in claim 3, wherein said spring device further includes a securement clip on said main support section for gripping said main support section to said front lower marginal section.

6. The sample tube rack as claimed in claim 5, wherein said individual upwardly extending spring arms have opposite side edges and one of said securement clips is provided at one of the opposite side edges of at least one of said spring arms.

7. The sample tube rack as claimed in claim 6, wherein each of said securement clips are provided at one of the opposite side edges of each of said spring arms.

8. The sample tube rack as claimed in claim 1, further including a latch securement pin and a latch securement opening, one of said latch securement pin and said latch securement opening being provided on said front lower marginal section and the other of said latch securement pin and said latch securement opening being provided on said spring device such that engagement between said latch securement pin and said latch securement opening helps locate said spring device on said lower front marginal section.

9. The sample tube rack as claimed in claim 8, wherein two of said securement pins are formed on said front lower marginal section and two of said securement openings are provided in said spring device for respective interengagement between the securement openings and the securement pins.

10. The sample tube rack as claimed in claim 1, wherein said rack further includes a transport securement appendage for attachment to an automatic transport device.

11. The sample tube rack as claimed in claim 10, wherein said transport securement appendage is provided at the bottom portion of each of said end walls and extend away from said end walls.

12. The sample tube rack as claimed in claim 10, wherein said transport securement appendage is provided on each of said end walls as a continuation of said rear wall and said transport appendage extends away from said end wall.

13. The sample tube rack as claimed in claim 1, further including a collection basin formed separately from said rack frame and detachably securable to said rack frame at the lower portion of said opposite end walls.

14. The sample tube rack as claimed in claim 13, wherein said collection basin includes opposite end walls corresponding to the opposite end walls of said rack frame and latching members are provided on the end walls of said rack frame and on the end walls of said collection basin for detachable engagement to detachably secure said collection basin to said rack frame.

15. The sample tube rack as claimed in claim 1, further including a base portion at the lower portion of said end walls of said rack frame.

16. A sample tube rack, comprising a one-piece frame having a top wall, a rear wall depending from said top wall and having a lower free edge, opposite end walls joined to said rear wall and having lower end portions depending from said top wall below the lower free edge of said rear wall, at least one partition member spaced between said end walls to define at least two sample tube chambers, said partition member having a lower end portion depending below the lower free edge of said rear wall, a front lower marginal section joining said end walls and said partition member, and a one-piece spring device joined to said front lower marginal section having individual upwardly extending spring arms each of which is inclined into a respective said sample tube chamber to bias said sample tube chamber toward said rear wall.

17. The sample tube rack as claimed in claim 16 wherein the top wall has sample tube openings and oppositely disposed riser portions formed with concave curved recesses that align with the sample tube openings in the top wall to conform with the upper periphery of a sample tube that is receivable in each of the sample tube chambers.

18. The sample tube rack claimed in claim 16, wherein actuator members for actuating a sample container dispenser are formed to extend upwardly from the top wall of the sample tube rack.

19. The sample tube rack claimed in claim 16, wherein each of said sample tube chambers has a tube cradle surface formed on the rear wall.

20. The sample tube rack claimed in claim 16, wherein said tube cradle surface includes two converging rear wall portions that are joined by an apex section of the rear wall.

* * * * *